United States Patent [19]

Schwing et al.

[11] 4,156,738
[45] May 29, 1979

[54] UREIDONITRILES USEFUL AS ANTIHYPERTENSIVES

[75] Inventors: Gregory W. Schwing, Lincoln University, Pa.; William A. Price, Jr.; Dewey H. Smith, Jr., both of Wilmington, Del.

[73] Assignee: E. I. Du Pont de Nemours and Company, Wilmington, Del.

[21] Appl. No.: 840,362

[22] Filed: Oct. 7, 1977

[51] Int. Cl.$^2$ ............... C07C 121/417; C07C 121/46; A01K 31/275
[52] U.S. Cl. .................. 424/304; 260/464; 260/465.4; 260/465.5 R; 260/465.6
[58] Field of Search .................. 424/304; 260/465.4, 260/464

[56] References Cited

U.S. PATENT DOCUMENTS

| 2,733,988 | 2/1956 | Searle | 260/465.4 X |
|---|---|---|---|
| 3,686,303 | 8/1972 | Knowles | 260/464 X |
| 3,803,208 | 4/1974 | Szabo | 260/465.4 X |
| 3,969,370 | 7/1976 | Dittmar | 424/279 X |
| 4,002,767 | 1/1977 | Aldrich et al. | 424/322 |
| 4,009,847 | 3/1977 | Aldrich et al. | 424/275 |

FOREIGN PATENT DOCUMENTS 50-69233  10/1973  Japan .................. 424/304

OTHER PUBLICATIONS

Gadekar et al., J. Med. Chem., 11 (1968), pp. 811–814.
Short et al., J. Med. Chem., 11 (1968), pp. 1129–1135.
Sturtevant, Annals of Internal Medicine, 49 (1958), pp. 1281–1293.
Friedman et al., Proc. Soc. Exp. Biol. and Med., 70, pp. 670–672.
Herbst et al., C. A., 26, 3779 (1932).
Biltz et al., C. A., 21, 1794 (1927).
Brown, C. A., 51, 12927 (1957).

*Primary Examiner*—Joseph Paul Brust

[57] ABSTRACT

Ureidonitriles, such as N-(1-cyano-1-methylethyl)-N'-(1,1-dimethylethyl)urea with antihypertensive activity in warm-blooded animals.

27 Claims, No Drawings

UREIDONITRILES USEFUL AS ANTIHYPERTENSIVES

BACKGROUND OF THE INVENTION

This invention relates to ureidonitriles useful as antihypertensives.

Certain guanidine derivatives of tert-carbinamines possess antihypertensive (hypotensive) activity. Specific examples are tert-alkyl cyanoguanidines such as described by S. M. Gadekar, S. Nibi, and E. Cohen, *J. Med. Chem.*, 11, 811 (1968); and various derivatives of tert-butyl guanidines as described by J. H. Short, C. W. Ours, W. J. Ranuse, Jr., *J. Med. Chem.*, 11, 1129 (1968). Urea derivatives are not represented in general reviews of antihypertensive agents. These reviews include W. T. Comer and A. W. Gomoll, Medicinal Chemistry, Third Edition, A. Burger, Wiley Interscience, New York, 1970, pp. 1019-1064 and Medicinal Chemistry, Volume 7, "Antihypertensive Agents," E. Schlittler, Academic Press, New York, 1967.

Recently several patents claiming 1-tert-alkyl-3-(substituted cyclohexenyl)ureas (U.S. Pat. No. 4,002,767), 1-tert-alkyl-3-(substituted thienyl)ureas (U.S. Pat. No. 4,009,847), and 1-tert-alkyl-3-(substituted furyl)ureas (U.S. Pat. No. 3,969,370) as antihypertensive agents have appeared. The compounds of this invention differ structurally from these compounds since, e.g. (1) none of the above compounds contain a nitrile moiety, and (2) in all of the above cases the urea group is attached to an enolizable heterocyclic or carbocyclic ring system.

Many current antihypertensives produce unwanted side effects because of their undesirable mechanism of action. For example, guanethidine is an adrenergic neuron blocker, mecamylamine is a ganglion blocker, phenoxybenzamine is an α-adrenergic receptor blocker, and reserpine is a catecholamine depletor. Each of these mechanisms of action is undesirable because of the serious side effects produced.

The compounds of this invention appear to lower blood pressure by a desirable mechanism of action—direct peripheral vasodilation—and, therefore have a distinct advantage over the above undesirably-acting antihypertensives.

Furthermore, these compounds do not appear to produce central nervous system effects such as those seen with clonidine and α-methyldopa administration.

SUMMARY OF THE INVENTION

This invention relates to compounds of Formula I, processes for their manufacture, compositions containing them, and methods of using them to treat hypertension in mammals.

$$R_4-\overset{R_3}{\underset{R_5}{\overset{|}{C}}}-\overset{H}{\underset{||}{\overset{|}{N}}}-\overset{H}{\underset{O}{\overset{|}{C}}}-\overset{R_1}{\underset{R_2}{\overset{|}{N}}}-\overset{}{\underset{}{\overset{|}{C}}}-CN \qquad I$$

where
$R_1$ is H, straight or branched alkyl of 1–3 carbon atoms or cyclopropyl;
$R_2$ is H, methyl or ethyl; or
$R_1$ and $R_2$ taken together are $-(CH_2)_n-$ where n is 3–4;
$R_3$ is methyl;
$R_4$ is methyl or ethyl;
$R_5$ is straight or branched alkyl or alkenyl of 1–3 carbon atoms; or
$R_4$ and $R_5$ taken together are $-(CH_2)_m-$ where m is 2–4;
with the proviso that when $R_1$ is isopropyl, $R_2$ is H.

PREFERRED EMBODIMENTS OF THE INVENTION

Preferred compounds of Formula I include those where:
$R_1$ is H and $R_2$ is ethyl;
$R_1$ is methyl and $R_2$ is either H, methyl or ethyl; and
$R_1$ is ethyl and $R_2$ is ethyl.

Additional preferred compounds include those where $R_3$ and $R_5$ are methyl and $R_4$ is methyl or ethyl.

More preferred are those compounds where $R_1$, $R_2$, $R_3$, $R_4$ and $R_5$ have the preferred definitions.

Specific examples of preferred compounds are those where:

| $R_1$ | $R_2$ | $R_3$ | $R_4$ | $R_5$ |
| --- | --- | --- | --- | --- |
| H | $CH_3$ | $CH_3$ | $CH_3$ | $CH_3$ |
| $CH_3$ | $CH_3$ | $CH_3$ | $CH_3$ | $CH_3$ |
| $CH_3$ | $CH_2CH_3$ | $CH_3$ | $CH_3$ | $CH_3$ |
| $CH_3$ | $CH_3$ | $CH_3$ | $CH_2CH_3$ | $CH_3$ |
| $CH_2CH_3$ | $CH_2CH_3$ | $CH_3$ | $CH_3$ | $CH_3$ |

SYNTHESIS

The compounds of this invention are prepared according to the following general reaction:

$$NH_2-\overset{R_1}{\underset{R_2}{\overset{|}{C}}}-CN + R_4-\overset{R_3}{\underset{R_5}{\overset{|}{C}}}-NCO \longrightarrow$$

$$R_4-\overset{R_3}{\underset{R_5}{\overset{|}{C}}}-NH-\overset{O}{\overset{||}{C}}-NH-\overset{R_1}{\underset{R_2}{\overset{|}{C}}}-CN$$

where $R_1$ to $R_5$ are as previously defined.

The reactants are contacted in a dry atmosphere in an inert organic solvent such as toluene, tetrahydrofuran or benzene at temperatures from 25° C. to the boiling point of the solvent, preferably from 60° C. to the boiling point of the solvent. Reaction time is usually one-half hour to six hours, preferably one and one-half hours to five hours. A basic catalyst such as pyridine may be used, but is not necessary; also optionally, the reaction can be run under an inert atmosphere such as nitrogen.

Methods for making the isocyanates are outlined as follows:

$$R_4-\overset{R_3}{\underset{R_5}{\overset{|}{C}}}-COOH + (CH_3CH_2)_3N +$$

$$CH_3CH_2OCCl + NaN_3 \longrightarrow R_4-\overset{R_3}{\underset{R_5}{\overset{|}{C}}}-NCO$$

See Kaiser and Weinstock, *Organic Synthesis*, 51 (1971), 48–52.

The acids are either commercially available or easily prepared by procedures known in the art.

Methods for making the aminonitriles are outlined as follows:

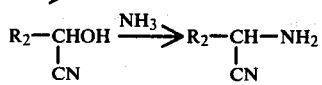

See Leitch and Linstead, *J. Chem. Soc.*, pt. 1 (1932), 451, for conversion to cyanohydrin, and Kustz and Disselnkötter, *Liebigs Ann. Chem.*, 764, (1972), 69–93, for conversion to aminonitriles.

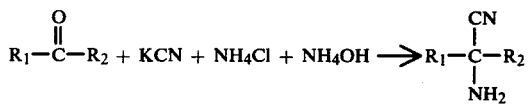

See U.S. Pat. No. 3,803,208, Karoly Szabo and Venkat Rao Ganti.

The aldehydes and ketones are commercially available or easily prepared by procedures known in the art.

To further illustrate the present invention, the following examples are provided. All temperatures are in degrees centigrade, all ratios are by volume, and all percentages are by weight unless otherwise indicated.

EXAMPLE 1

2-Hydroxypropionitrile

To a stirring solution of 104.6 g. (1 mole) of sodium bisulfite in 200 ml. of water in a water/ice bath, there is slowly added 29.5 g. (0.67 mole) acetaldehyde. The resulting mixture is refrigerated overnight. At the end of this period, a solution of 32.6 g. (0.67 mole) sodium cyanide in 70 ml. of water is slowly added to the stirring mixture, keeping the temperature below 15°. The resulting mixture is allowed to stand overnight. At the end of this period, the solid is filtered out and the filtrate extracted several times with ether. The solid is also washed several times with ether and the ether layers combined, dried over sodium sulfate, filtered and the ether removed at reduced pressure. The residue is stabilized with a few drops of concentrated sulfuric acid, and distilled under reduced pressure to give 2-hydroxypropionitrile, b.p. 58° at 2.0 mm Hg.

EXAMPLES 2–4

The procedure of Example 1 is repeated substituting an equivalent amount of the listed "Aldehyde" for the acetaldehyde of Example 1 to obtain the indicated "Product".

| Example | Aldehyde | Product |
|---|---|---|
| 2 | CH$_3$CH$_2$CHO | CH$_3$CH$_2$CH(OH)(CN), b.p. 62° at 1.2 mm Hg. |
| 3 | CH$_3$CH$_2$CH$_2$CHO | CH$_3$CH$_2$CH$_2$CH(OH)(CN), b.p. 86° at 4.3 mm Hg. |
| 4 | CH$_3$CH(CH$_3$)CHO | (CH$_3$)$_2$CHCH(OH)(CN), b.p. 79° at 2.7 mm Hg. |

EXAMPLES 5–8

The cyanohydrins listed below were converted to the corresponding aminonitriles by the procedures of P. Kurtz and H. Disselnkötter, *Liebigs Ann. Chem.*, 764 69–93 (1972).

| Example | Cyanohydrin | Aminonitrile |
|---|---|---|
| 5 | CH$_3$CH(OH)CN | CH$_3$CH(NH$_2$)CN |
| 6 | CH$_3$CH$_2$CH(OH)CN | CH$_3$CH$_2$CH(NH$_2$)CN |
| 7 | CH$_3$CH$_2$CH$_2$CH(OH)CN | CH$_3$CH$_2$CH$_2$CH(NH$_2$)CN |
| 8 | (CH$_3$)$_2$CHCH(OH)CN | (CH$_3$)$_2$CHCH(NH$_2$)CN |

EXAMPLE 9

N-(1-Cyanoethyl)-N'-(1,1-dimethylethyl)urea

To a stirring solution of 21.1 g (0.3 mole) 2-aminopropionitrile in 300 ml. dry tetrahydrofuran under a nitrogen atmosphere, there is added 30.7 g (0.3 mole) t-butyl isocyanate (97%). The resulting mixture is heated at reflux for five hours. At the end of this period, the tetrahydrofuran is removed at reduced pressure. The solid is recrystallized from methanol:water, 60:40, to give N-(1-cyanoethyl)-N'-(1,1-dimethylethyl)urea, m.p. 161°–3°.

Anal. Calcd. for C$_8$H$_{15}$N$_3$O: C: 56.79, H: 8.93, N: 24.83; Found: C: 56.70, 56.49, H: 8.43, 8.69, N: 24.99, 24.99.

EXAMPLES 10–12

The procedure of Example 9 is repeated substituting an equivalent amount of the listed "Nitrile" for the 2-aminopropionitrile of Example 9 to obtain the indicated "Product."

| Example | Nitrile | Product |
|---|---|---|
| 10 | CH$_3$CH$_2$CH(NH$_2$)CN | (CH$_3$)$_3$C—NH—C(O)—NH—CH(CH$_2$CH$_3$)—CN, m.p. 120°–1° |
| 11 | CH$_3$CH$_2$CH$_2$CH(NH$_2$)CN | (CH$_3$)$_3$C—NH—C(O)—NH—CH(CN)—CH$_2$CH$_2$CH$_3$, m.p. 95°–6° |
| 12 | (CH$_3$)$_2$CHCH(NH$_2$)CN | (CH$_3$)$_3$C—NHCNH—CH(CN)—CH(CH$_3$)—CH$_3$, m.p. 149°–50° |

EXAMPLE 13

N-Cyanomethyl-N'-(1,1-dimethylethyl)urea

To a stirring mixture of 18.7 g (0.2 mole) aminoacetonitrile·HCl in 300 ml. dry tetrahydrofuran under a nitrogen atmosphere, there is added 20.4 g. (0.2 mole) t-butyl isocyanate (97%), followed by 28 ml. (0.2 mole) triethylamine. The resulting mixture is heated at reflux for five hours, cooled and the tetrahydrofuran removed at reduced pressure. The solid is recrystallized from ethyl acetate to give N-cyanomethyl-N'-(1,1-dimethylethyl)urea, m.p. 128°-32° (Anal. Calcd. for $C_7H_{13}N_3O$: C: 54.17, H: 8.44, N: 27.07; Found: C: 53.84, H: 8.33, N: 26.86.

EXAMPLE 14

2-Methyl-2-aminopropionitrile

To a stirring solution of 205.1 g. (3.15 moles) potassium cyanide in 360 ml. of water, there is added a mixture of 183.0 g. (3.42 moles) ammonium chloride in 420 ml. of water. To the resulting mixture, there is added 201 ml. (3.0 moles) ammonium hydroxide, followed by 222 ml. (3.0 moles) acetone. The resulting mixture is stirred for one-half hour. At the end of this period, the mixture is held between 45° and 55° for 18 hours. At the end of this period, the mixture is extracted several times with ether. The ether portions are combined and dried. The ether is removed at reduced pressure to give the product 2-methyl-2-aminopropionitrile. The product is used without further purification. (This procedure follows that of U.S. Pat. No. 3,803,208-Karoly Szabo and Venkat Rao Ganti).

EXAMPLES 15-20

The procedure of Example 9 is repeated substituting an equivalent amount of the listed "Ketone" for the acetone of Example 14 to obtain the indicated "Product".

| Example | Ketone | Product |
|---|---|---|
| 15 | $CH_3-\underset{\underset{O}{\|\|}}{C}-CH_2CH_3$ | $CH_3-\underset{\underset{CN}{\|}}{C(NH_2)}-CH_2CH_3$ |
| 16 | $CH_3CH_2-\underset{\underset{O}{\|\|}}{C}-CH_2CH_3$ | $CH_3CH_2-\underset{\underset{CN}{\|}}{C(NH_2)}-CH_2CH_3$ |
| 17 | $CH_3-\underset{\underset{O}{\|\|}}{C}-\overset{CH-CH_2}{\underset{CH_2}{\diagdown\diagup}}$ | $CH_3-\underset{\underset{CN}{\|}}{C(NH_2)}-\overset{CH-CH_2}{\underset{CH_2}{\diagdown\diagup}}$ |
| 18 | $CH_3CH_2-\underset{\underset{O}{\|\|}}{C}-CH_2CH_2CH_3$ | $CH_3CH_2-\underset{\underset{CN}{\|}}{C(NH_2)}-CH_2CH_2CH_3$ |
| 19 | $\begin{array}{c}CH_2-C=O\\ \|\quad\|\\ CH_2-CH_2\end{array}$ | $\begin{array}{c}\quad\quad NH_2\\ \quad\quad \|\\ CH_2-C-CN\\ \|\quad\quad\|\\ CH_2-CH_2\end{array}$ |
| 20 | $H_2C\underset{CH_2-CH_2}{\overset{CH_2-C=O}{\diagup\diagdown}}$ | $H_2C\underset{CH_2-CH_2}{\overset{CH_2-C(NH_2)CN}{\diagup\diagdown}}$ |

EXAMPLE 21

N-(1-Cyano-1-methylethyl)-N'-(1,1-dimethylethyl)urea

In a nitrogen atmosphere, 24.8 g. (0.3 mole) 2-methyl-2-aminopropionitrile and 30.7 g. (0.3 mole) t-butyl isocyanate, 97%, are combined and stirred for 5 minutes. At the end of this period, the mixture is filtered and 1 ml. of pyridine is added to the filtrate. This mixture is heated in an oil bath for one and one-half hours, keeping the temperature of the bath below 70°. The solid is recrystallized from methanol:water, 60:40, to give N-(1-cyano-1-methylethyl)-N'-(1,1-dimethylethyl)urea, m.p. 204°-5°; Anal. Calcd. for $C_9H_{17}N_3O$; C: 58.99, H: 9.35, N: 22.93; Found: C: 59.21, H: 9.26, N: 22.59.

EXAMPLES 22-25

The procedure of Example 21 is repeated substituting an equivalent amount of the listed "Aminonitrile" for the 2-methyl-2-aminopropionitrile of Example 21 to obtain the indicated product.

| Example | Aminonitrile | Product |
|---|---|---|
| 22 | $CH_3-\underset{\underset{CN}{\|}}{C(NH_2)}-CH_2CH_3$ | $CH_3-\underset{\underset{CH_3}{\|}}{\overset{\overset{CH_3}{\|}}{C}}-NH-\overset{O}{\underset{\|\|}{C}}-NH-\underset{\underset{CN}{\|}}{\overset{\overset{CH_3}{\|}}{C}}-CH_2CH_3$ m.p. 201°-2° |
| 23 | $CH_3CH_2-\underset{\underset{CN}{\|}}{C(NH_2)}-CH_2CH_3$ | $CH_3-\underset{\underset{CH_3}{\|}}{\overset{\overset{CH_3}{\|}}{C}}-NH-\overset{O}{\underset{\|\|}{C}}-NH-\underset{\underset{CN}{\|}}{\overset{\overset{CH_2CH_3}{\|}}{C}}-CH_2CH_3$ m.p. 183°-5° |
| 24 | $CH_3-\underset{\underset{CN}{\|}}{C(NH_2)}-\overset{CH-CH_2}{\underset{CH_2}{\diagdown\diagup}}$ | $CH_3-\underset{\underset{CH_3}{\|}}{\overset{\overset{CH_3}{\|}}{C}}-NH-\overset{O}{\underset{\|\|}{C}}-NH-\underset{\underset{CN}{\|}}{\overset{\overset{CH_3}{\|}}{C}}-\overset{CH-CH_2}{\underset{CH_2}{\diagdown\diagup}}$ m.p. 190°-1° |

-continued

| Example | Aminonitrile | Product |
|---------|--------------|---------|
| 25 | CH₃—CH₂—C(NH₂)—CH₂CH₂CH₃<br>            \|<br>            CN | $\text{CH}_3\text{-}\underset{\underset{\text{CH}_3}{\|}}{\overset{\overset{\text{CH}_3}{\|}}{\text{C}}}\text{-NH-}\overset{\overset{\text{O}}{\|}}{\text{C}}\text{-NH-}\underset{\underset{\text{CN}}{\|}}{\overset{\overset{\text{CH}_2\text{CH}_3}{\|}}{\text{C}}}\text{-CH}_2\text{CH}_2\text{CH}_3$    m.p. 141°–3° |

EXAMPLE 26

N-(1-Cyanocyclobutyl-)-N'-(1,1-dimethylethyl)urea

In a nitrogen atmosphere, 9.6 g. (0.1 mole) cyclobutylaminonitrile and 10.2 g. (0.1 mole) t-butyl isocyanate, 97%, are combined and stirred. After 5 minutes, 1 ml. of pyridine is added and the resulting mixture heated in an oil bath for one and one-half hours, keeping the bath temperature below 70°. The solid is recrystallized first from acetonitrile and second from ether/methanol to give the product, N-(1-cyanocyclobutyl)-N'-(1,1-dimethylethyl)urea, m.p. 212°–4°. Anal. Calcd. for $C_{10}H_{17}N_3O$: C: 61.51, H: 8.78, N: 21.52; Found: C: 61.76, 61.72, H: 8.41, 8.49, N: 21.73, 21.61.

EXAMPLE 27

The procedure of Example 26 is repeated substituting an equivalent amount of cyclopentylaminonitrile for the cyclobutylaminonitrile of Example 26 to obtain N-(1-cyanocyclopentyl)-N'-(1,1-dimethylethyl)urea, m.p. 206°–7°.

EXAMPLE 28

N-(1-Cyanoethyl)-N'-(1,1-dimethylpropyl)urea

To a stirring solution of 23.5 g (0.2 mole) 2,2-dimethylbutanoic acid in 150 ml. acetone, there is added 30 ml. triethylamine. The temperature is lowered to 0°, and 21.1 ml. (0.22 mol) ethyl chloroformate are added over one-half hour, keeping the temperature at 0°. At the end of the addition, the mixture is stirred for 15 minutes, keeping the temperature at 0°. At the end of this period, a solution of 26.0 g. (0.4 mole) sodium azide in 75 ml. of water is added over one-half hour, keeping the temperature at 0°. The resulting mixture is stirred one hour at 0°. At the end of this period, the mixture is poured into 750 ml. of ice water. This mixture is extracted 4 times with 200 ml. toluene. The toluene portions are combined and dried. The toluene solution is added dropwise to 150 ml. of toluene refluxing in a nitrogen atmosphere. After the addition is complete, the solution is heated to reflux until the IR shows the disappearance of the azide peak (about two and one-half hours). The solution is then cooled and 14.0 g. (0.2 mole) 2-aminopropionitrile are added. The resulting mixture is refluxed for 5 hours. At the end of this period, the toluene is removed at reduced pressure. The residue is put through a column of Silica AR CC7 using toluene:ethyl acetate, 80:20 as the liquid phase. The desired portions are combined and the toluene and ethyl acetate are removed under reduced pressure. The residue is recrystallized from ethyl acetate/cyclohexane to give the product, N-(1-cyanoethyl)-N'-(1,1-dimethylpropyl)urea, m.p. 129°–30°. Anal. Calcd. for $C_8H_{17}N_3O$: C: 58.99, H: 9.35, N: 22.93; Found: C: 58.82, H: 9.13, N: 22.92.

EXAMPLES 29–36

The procedure of Example 28 is repeated substituting an equivalent amount of the listed "Isocyanate" for the t-amyl isocyanate of Example 28 and an equivalent amount of the listed "Aminonitrile" for the 2-aminopropionitrile of Example 28 to obtain the indicated product.

| Example | Isocyanate | Aminonitrile | Product |
|---------|------------|--------------|---------|
| 29 | CH₃CH₂—C(CH₃)(CH₃)—NCO | CH₃C(CN)(CH₃)(NH₂) | CH₂(CH₃)—C(CH₃)—NH—C(=O)—NH—C(CH₃)(CH₃)—CN   m.p. 196–7° |
| 30 | CH₃CH₂—C(CH₃)(CH₂CH₃)—NCO | CH₃C(CN)(CH₃)(NH₂) | CH₂(CH₃)—C(CH₂CH₃)—NH—C(=O)—NH—C(CH₃)(CH₃)—CN   m.p. 200–1° |
| 31 | CH₃CH₂—C(CH₃)(CH₂CH₃)—NCO | CH₃CH(CN)(NH₂) | CH₃CH₂—C(CH₃)(CH₂CH₃)—NH—C(=O)—NH—CH(CH₃)—CN |
| 32 | cyclobutyl-NCO (1-isocyanato-1-methylcyclobutane: CH₂—CH₂—C(CH₃)(NCO)—CH₂—CH₂) | CH₃C(CH₃)(CN)(NH₂) | cyclobutyl-C(CH₃)—NH—C(=O)—NH—C(CH₃)(CH₃)—CN   m.p. 203–4° |
| 33 | CH₃CH₂CH₂C(CH₃)(CH₃)—NCO | CH₃C(CH₃)(CN)(NH₂) | CH₃CH₂CH₂C(CH₃)(CH₃)—NH—C(=O)—NH—C(CH₃)(CH₃)—CN   m.p. 159–160° |
| 34 | CH₃CH₂CH₂—C(CH₃)(CH₃)—NCO | CH₃CH(CN)(NH₂) | CH₃CH₂CH₂C(CH₃)(CH₃)—NH—C(=O)—NH—CH(CH₃)—CN |

-continued

| Example | Isocyanate | Aminonitrile | Product |
|---------|-----------|--------------|---------|
| 35 | $CH_2=CH-CH_2-\underset{\underset{CH_3}{|}}{\overset{\overset{CH_3}{|}}{C}}-NCO$ | $CH_3-\underset{\underset{NH_2}{|}}{\overset{\overset{CH_3}{|}}{C}}-CN$ | $CH_2=CH-CH_2-\underset{\underset{CH_3}{|}}{\overset{\overset{CH_3}{|}}{C}}-NH-\underset{\underset{O}{\|}}{C}-NH-\underset{\underset{CH_3}{|}}{\overset{\overset{CH_3}{|}}{C}}-CN$ <br> m.p. 165–6° |
| 36 | $CH_2=CH-CH_2-\underset{\underset{CH_3}{|}}{\overset{\overset{CH_3}{|}}{C}}-NCO$ | $CH_3CHCN$ <br> $\quad\quad\;\;\:\mid$ <br> $\quad\quad\;\;\:NH_2$ | $CH_2=CH-CH_2-CHNH\overset{\overset{O}{\|}}{C}$ <br> $\qquad\qquad\qquad\qquad\quad\;\;\mid\;\;\;\;\;\;\;\;\;\;\;\;\mid$ <br> $\qquad\qquad\qquad\qquad\;CH_3\;\;\;\;\;NH$ <br> $\qquad\qquad\qquad\qquad\qquad\qquad\;\mid$ <br> $\qquad\qquad\qquad\qquad\qquad\;\;\;HC-CH_3$ <br> $\qquad\qquad\qquad\qquad\qquad\qquad\;\mid$ <br> $\qquad\qquad\qquad\qquad\qquad\qquad\;CN$ <br> m.p 98–101° |

Administration and Dosage

The compounds of this invention can be administered in the treatment of hypertension by any means that effects contact of the active ingredient compound with the site of action in the mammal. For example, administration can be parenteral, i.e., subcutaneous, intravenous, intramuscular, or intraperitoneal. Alternatively or concurrently, administration can be by the oral route.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1 to 50 milligrams per kilogram of body weight. Ordinarily, from 0.5 to 40, and preferably 1.0 to 20, milligrams per kilogram per day in one or more applications per day is effective to obtain desired results. For the more potent compounds of the invention, the daily dosage ranges are from about 0.1 to 10 mg/kg, preferably 0.5 to 10 mg/kg, and more preferably 0.5 to 5 mg/kg.

The antihypertensive activity of the compounds of this invention is evidenced by tests conducted in hypertensive rats and by further tests which show a blood pressure lowering effect in normotensive dogs.

In these tests rats are made hypertensive by subcutaneous implantation of pellets of desoxycorticosterone acetate (DOCA) and by giving the rats saline solution to drink essentially according to the method described by Sturtevant [*Annals of Internal Medicine,* 49, 1281 (1958)]. Graded dose levels of each compound are administered orally to groups of 8 hypertensive rats. The compound is prepared in an aqueous polyvinyl alcohol-/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by modification of the microphone-manometer technique [Friedman, M. and Freed, S. C., *Proc. Soc. Exp. Biol. and Med.,* 70, 670 (1949)]. That dose of compound which produces a 30 mm mercury (mm Hg) reduction in blood pressure when compared to the mean systolic arterial blood pressure of the control animals is then determined (Effective Dose 30). For example, an $ED_{30}$ of 1.1 mg/kg orally was obtained with N-(1-cyano-1-methylethyl)-N'-(1,1-dimethylethyl)urea, $ED_{30}$'s of 1.2, 1.4, 1.9, and 2.2 were obtained with N-(1-cyano-1-methylethyl)-N'-(1,1-dimethylpropyl)urea, N-(1-cyanoethyl)-N'-(1,1-dimethylethyl)urea, N-(1-cyano-1-methylpropyl)-N'-(1,1-dimethylethyl)urea, and N-(1-cyano-1-ethylpropyl)-N'-(1,1-dimethylethyl)urea respectively.

In a test involving dogs, N-(1-cyano-1-methylethyl)-N'-(1,1-dimethylethyl)urea is administered intravenously to 8 anesthetized normotensive dogs according to a cumulative dose schedule. Arterial blood pressure is recorded directly through an arterial cannula and a polygraph by which it is determined that the compound shows statistically significant blood pressure lowering in comparison to the predosing control value and to the effect of vehicle on control animals.

The compounds of this invention can be employed in useful pharmaceutical compositions such as injectables, oral dosage forms such as tablets, hard gelatin capsules, soft gelatin capsules and aqueous suspensions.

The compounds of this invention have a therapeutic dose range in man from 0.1 to 50 mg./kg./day; some of the more preferred compounds will have a dose range from 0.1 to 10 mg./kg./day and the most preferred dose range will be from 0.5 to 5 mg./kg./day. The dosage forms described are designed to deliver this therapeutic dose.

Hard Capsules

Hard gelatin capsules are prepared by filling standard two-piece hard gelatin capsules with the following mixture using conventional encapsulating equipment:

| | |
|---|---|
| Active Compound | 100 mg. |
| Lactose | 225 mg. |
| Talc | 25 mg. |
| Magnesium Stearate | 8 mg. |

Soft Capsules

Mixtures containing 100 mg. active compound in Polysorbate 80–150 mg., Glycerin—15 mg., and Purified Water—8 mg., are prepared and injected by means of a positive displacement pump in gelatin to form soft gelatin capsules. A soft gelatin capsule will contain 100 mg. of active compound. The capsules are washed in petroleum ether and dried.

Tablets

Tablets are prepared by conventional procedures so that each tablet will contain:

| | |
|---|---|
| Active Compound | 100 mg. |
| Spray Dried Lactose | 300 mg. |
| Microcrystalline Cellulose | 30 mg. |
| Polyvinylpyrrolidone | 3 mg. |

-continued

| | |
|---|---|
| Magnesium Stearate | 4 mg. |

Aqueous Suspension

An aqueous suspension for oral administration is prepared so that each 5 ml. contains:

| | |
|---|---|
| Active Compound | 100 mg. |
| Carboxy Methyl Cellulose | 5% |
| Syrup | 35% |
| Glycerin | 10% |
| Sorbitol | 10% |
| Methyl Cellulose | 5% |
| Sodium Benzoate | 5 mg. |
| Flavor | .1 % |
| Water Q.S. | 5 cc |

Parenteral Composition

A parenteral composition suitable for intra-muscular administration is prepared so that each ml. contains:

| | | |
|---|---|---|
| Active Compound | 100 | mg. |
| Polysorbate 80 | 1 | mg. |
| Sodium Chloride - add enough quantity to make isotonic solution | | |
| Benzyl Alcohol | 1.5 | % |
| Water for Inj., Q.S. | 1 | ml. |

Suppositories

A suitable number of suppositories is prepared so that each suppository contains:

| | |
|---|---|
| Active Compound | 100 mg. |
| Polyethylene Glycol 4000 | 1.5 g |
| Polyethylene Glycol 1000 | 1.5 g |

The polyethylene glycol 4000 and polyethylene glycol 1000 are melted followed by addition of the active compound while mixing. This composition is poured into suppository molds followed by cooling.

A wide variety of other pharmaceutical carriers, diluents, and additives can be used. These are described in "Remington's Pharmaceutical Sciences" by E. W. Martin, a well-known reference in this field.

What is claimed is:

1. A compound of the formula $$R_4 - \underset{\underset{R_5}{|}}{\overset{\overset{R_3}{|}}{C}} - \underset{\underset{O}{\|}}{\overset{\overset{H}{|}}{N}} - C - \underset{\underset{R_2}{|}}{\overset{\overset{H}{|}}{N}} - \overset{\overset{R_1}{|}}{C} - CN$$

where
$R_1$ is H, straight or branched alkyl of 1-3 carbon atoms or cyclopropyl;
$R_2$ is H, methyl or ethyl; or
$R_1$ and $R_2$ taken together are $-(CH_2)_n-$ where n is 3-4;
$R_3$ is methyl;
$R_4$ is methyl or ethyl;
$R_5$ is straight or branched alkyl or alkenyl of 1-3 carbon atoms, or
$R_4$ and $R_5$ taken together are $-(CH_2)_m-$ where m is 2-4;
with the proviso that when $R_1$ is isopropyl, $R_2$ is H.

2. The compound of claim 1 wherein $R_1$ is H and $R_2$ is ethyl.

3. The compound of claim 1 wherein $R_1$ is methyl and $R_2$ is H, methyl or ethyl.

4. The compound of claim 1 wherein $R_1$ is ethyl and $R_2$ is ethyl.

5. The compound of claim 1 wherein $R_1$ is H and $R_2$, $R_3$, $R_4$ and $R_5$ are methyl.

6. The compound of claim 1 wherein $R_1$, $R_2$, $R_3$, $R_4$ and $R_5$ are methyl.

7. The compound of claim 1 wherein $R_1$, $R_3$, $R_4$ and $R_5$ are methyl and $R_2$ is ethyl.

8. The compound of claim 1 wherein $R_1$, $R_2$, $R_3$ and $R_5$ are methyl and $R_4$ is ethyl.

9. The compound of claim 1 wherein $R_1$ and $R_2$ are ethyl and $R_3$, $R_4$ and $R_5$ are methyl.

10. A pharmaceutical composition useful for treating hypertension in a mammal consisting essentially of an antihypertensive effective amount of a compound of claim 1 and a pharmaceutically suitable carrier.

11. A pharmaceutical composition useful for treating hypertension in a mammal consisting essentially of an antihypertensive effective amount of a compound of claim 2 and a pharmaceutically suitable carrier.

12. A pharmaceutical composition useful for treating hypertension in a mammal consisting essentially of an antihypertensive effective amount of a compound of claim 3 and a pharmaceutically suitable carrier.

13. A pharmaceutical composition useful for treating hypertension in a mammal consisting essentially of an antihypertensive effective amount of a compound of claim 4 and a pharmaceutically suitable carrier.

14. A pharmaceutical composition useful for treating hypertension in a mammal consisting essentially of an antihypertensive effective amount of a compound of claim 5 and a pharmaceutically suitable carrier.

15. A pharmaceutical composition useful for treating hypertension in a mammal consisting essentially of an antihypertensive effective amount of a compound of claim 6 and a pharmaceutically suitable carrier.

16. A pharmaceutical composition useful for treating hypertension in a mammal consisting essentially of an antihypertensive effective amount of a compound of claim 7 and a pharmaceutically suitable carrier.

17. A pharmaceutical composition useful for treating hypertension in a mammal consisting essentially of an antihypertensive effective amount of a compound of claim 8 and a pharmaceutically suitable carrier.

18. A pharmaceutical composition useful for treating hypertension in a mammal consisting essentially of an antihypertensive effective amount of a compound of claim 9 and a pharmaceutically suitable carrier.

19. A method for treating hypertension in a mammal which comprises administering to the mammal an antihypertensive effective amount of a compound of claim 1.

20. A method for treating hypertension in a mammal which comprises administering to the mammal an antihypertensive effective amount of a compound of claim 2.

21. A method for treating hypertension in a mammal which comprises administering to the mammal an antihypertensive effective amount of a compound of claim 3.

22. A method for treating hypertension in a mammal which comprises administering to the mammal an antihypertensive effective amount of a compound of claim 4.

23. A method for treating hypertension in a mammal which comprises administering to the mammal an antihypertensive effective amount of a compound of claim 5.

24. A method for treating hypertension in a mammal which comprises administering to the mammal an antihypertensive effective amount of a compound of claim 6.

25. A method for treating hypertension in a mammal which comprises administering to the mammal an antihypertensive effective amount of a compound of claim 7.

26. A method for treating hypertension in a mammal which comprises administering to the mammal an antihypertensive effective amount of a compound of claim 8.

27. A method for treating hypertension in a mammal which comprises administering to the mammal an antihypertensive effective amount of a compound of claim 9.

* * * * *